United States Patent [19]

Rosenberg et al.

[11] Patent Number: 4,572,724
[45] Date of Patent: Feb. 25, 1986

[54] BLOOD FILTER

[75] Inventors: David J. Rosenberg, Glen Head; Vlado I. Matkovich, Glen Cove, both of N.Y.

[73] Assignee: Pall Corporation, Glen Cove, N.Y.

[21] Appl. No.: 599,585

[22] Filed: Apr. 12, 1984

[51] Int. Cl.⁴ ............................................. B01D 19/00
[52] U.S. Cl. ....................................... 55/159; 55/178; 55/204; 128/DIG. 3; 210/436; 210/472; 604/126
[58] Field of Search ................. 55/159, 185, 186, 187, 55/318, 204, 178; 128/DIG. 3; 210/321.4, 436, 472, 927, 512.1; 604/4, 5, 122, 126

[56] References Cited

U.S. PATENT DOCUMENTS

| | | | |
|---|---|---|---|
| 3,523,408 | 8/1970 | Rosenberg | 55/159 |
| 3,631,654 | 1/1972 | Riely | 55/159 |
| 3,701,433 | 10/1972 | Krakauer et al. | 210/436 |
| 3,778,971 | 12/1973 | Granger et al. | 55/159 |
| 3,803,810 | 4/1974 | Rosenberg | 55/159 |
| 3,827,562 | 8/1974 | Esmond | 604/406 X |
| 3,854,907 | 12/1974 | Rising | 55/159 |
| 3,891,416 | 6/1975 | Leonard et al. | 55/178 |
| 3,935,111 | 1/1976 | Bentley | 210/927 X |
| 3,967,628 | 7/1976 | Noiles | 604/126 |
| 4,013,072 | 3/1977 | Jess | 128/214 |
| 4,017,279 | 4/1977 | Bowley | 55/178 |
| 4,031,891 | 6/1977 | Jess | 128/214 |
| 4,046,696 | 9/1977 | Mouwen | 210/927 X |
| 4,262,668 | 4/1981 | Schmidt | 128/214 |
| 4,265,762 | 5/1981 | Brenholt | 210/321 |
| 4,276,170 | 6/1981 | Vaillancourt | 210/436 |
| 4,278,084 | 7/1981 | Pope | 128/214 |
| 4,298,358 | 11/1981 | Ruschke | 55/185 |
| 4,326,957 | 4/1982 | Rosenberg | 210/436 |
| 4,336,036 | 6/1982 | Leeke et al. | 55/159 |
| 4,344,777 | 8/1982 | Siposs | 55/178 |
| 4,345,919 | 8/1982 | Wilkinson et al. | 55/41 |
| 4,411,783 | 10/1983 | Dickens et al. | 210/304 |

Primary Examiner—Charles Hart
Attorney, Agent, or Firm—Leydig, Voit & Mayer, Ltd.

[57] ABSTRACT

A blood filter such as may be used in a cordiopulmonary bypass system includes a housing having upper and lower chambers with a cylindrical filter element disposed in the lower chamber. The inlet to the housing is in the upper chamber, which is upstream of the lower chamber, and the outlet is through the lower chamber and communicates with the interior of the filter element. Thus, blood enters the upper chamber and flows to the lower chamber where it passes through the filter element from the outer side to the interior to remove microemboli such as gas bubbles, fat emboli and agglomerates, the filtered blood exiting through the outlet. In order to remove a substantial amount of the gas in the blood, and particularly gross bubbles, upstream of the filter element, the upper chamber is cylindrical and the inlet directs the blood tangentially to flow around the periphery of the chamber. An annular baffle extending around a major portion of the chamber maintains the peripheral flow which produces a centrifugal action causing the blood to flow at the wall of the chamber and the gas to separate and move to the central portion where it is vented through a hydrophobic membrane covering the central portion of the top wall of the chamber. Blood from the periphery of the upper chamber flows down to the lower chamber through a sponge ring which removes additional gas bubbles by causing the latter to coalesce into larger bubbles which move radially inwardly of the ring and rise to the upper chamber where they also are vented through the membrane. Any gas bubbles which remain in the blood and which are larger than the acceptable size are blocked by the filter element. The bubbles at the filter element eventually coalesce into larger bubbles which break away from the filter element and rise to the upper chamber where they are vented through the membrane.

17 Claims, 9 Drawing Figures

BLOOD FILTER

BACKGROUND OF THE INVENTION

This invention relates to improvements in filters for use in the filtration of blood such as in cardiopulmonary bypass system used during open heart surgery. U.S. Pat. No. 3,701,433 discloses a disposable blood filter employing a woven mesh having a pore size within the range of 25 to 50 microns for removal of, *inter alia,* microemboli from artificially oxygenated blood prior to reintroduction into a patient during a cardiopulmonary bypass. Such filters marketed by Pall Corporation, the present assignee, and similar filters marketed by numerous others have proven highly effective and beneficial and are now universally employed during surgery involving cardiopulmonary bypass.

For well known medical reasons which need not be discussed here, it is absolutely critical that no free gas, whether in the form of microemboli or gross bubbles, be present in the blood returned to a patient. While most commercial filters are fairly effective in removing microemboli from an otherwise steady flow of blood, none of the commercial filters presently on the market can automatically assure that gross amounts of air presented to the upstream side of the filter element will not pass through the element and into the patient's blood stream. While a fine pore filter element fully wetted with blood is effective to prevent passage of a gas at a given limited rate, this effectiveness decreases dramatically when this rate is exceeded. Accordingly, one operating protocol requires a technician to continually monitor the blood filter, prepared to take emergency measure to assure that air does not accumulate upstream of the filter element and expose the filter to the gas rather than blood. Most filters of the type disclosed in U.S. Pat. No. 3,701,433 and used commercially include a port which may be employed to vent the gas but the port size typically is such that it is inadequate to vent a 100 per cent gas flow as when the blood feed to the pump is interrupted. With such an occurrence, at a flow rate of six liters per minute, the exterior chamber of a blood filter of the type shown in FIG. 4 of U.S. Pat. No. 3,701,433 will fill with gas in approximately two seconds and, shortly thereafter, air is likely to pass through the filter element and into a patient. Accordingly, a filter which quickly, automatically and safely vents all of the air presented at the upstream chamber, even in the event of a catastrophic failure, is highly desirable both in terms of safety to the patient and economy in use of resources and personnel.

SUMMARY OF THE INVENTION

The general object of the invention is to provide a new and improved blood filter for use in a cardiopulmonary bypass system in which a significant portion of the gas dispersed in the blood is removed in the upstream chamber and this gas, even when delivered in gross amounts, is automatically vented to the atmosphere before the gas reaches the filter element, the gas bubbles remaining in the blood being in such amount and size as to be readily captured by the filter element.

A more detailed object is to achieve the foregoing by causing the blood to flow in a circular path in the upstream chamber and produce a centrifugal action which causes the blood to flow at the periphery of the chamber while the gas separates and moves to the center portion of the chamber and is vented to the atmosphere through a hydrophobic membrane.

Still a further object is to achieve the circular flow of blood by introducing the blood tangentially into the upstream chamber and generally conforming the flow to the peripheral portion of the chamber while permitting the separated gas to move to the central portion.

Another object is to achieve rapid and automatic venting of the gas by locating the hydrophobic membrane in the top wall of the upstream chamber with the membrane overlying at least a substantial part of the central portion of the chamber.

It is also an object to coalesce at least some of the smaller gas bubbles remaining in the blood as the latter approaches the filter element thereby to form somewhat larger bubbles which are more easily removed.

Another object is to coalesce air bubbles by forcing a flow through a body of sponge material treated to retain and collect smaller bubbles until a plurality of them have formed a larger bubble which escapes the sponge material.

A further object is to provide a path separate from the sponge body for the larger bubbles as formed by coalescence to return to the upstream chamber and be vented through the hydrophobic member.

These and other objects will be apparent from the following detailed description with reference to the drawings.

DETAILED DESCRIPTION OF THE PREFERRED EMBODIMENT

Figure 1:
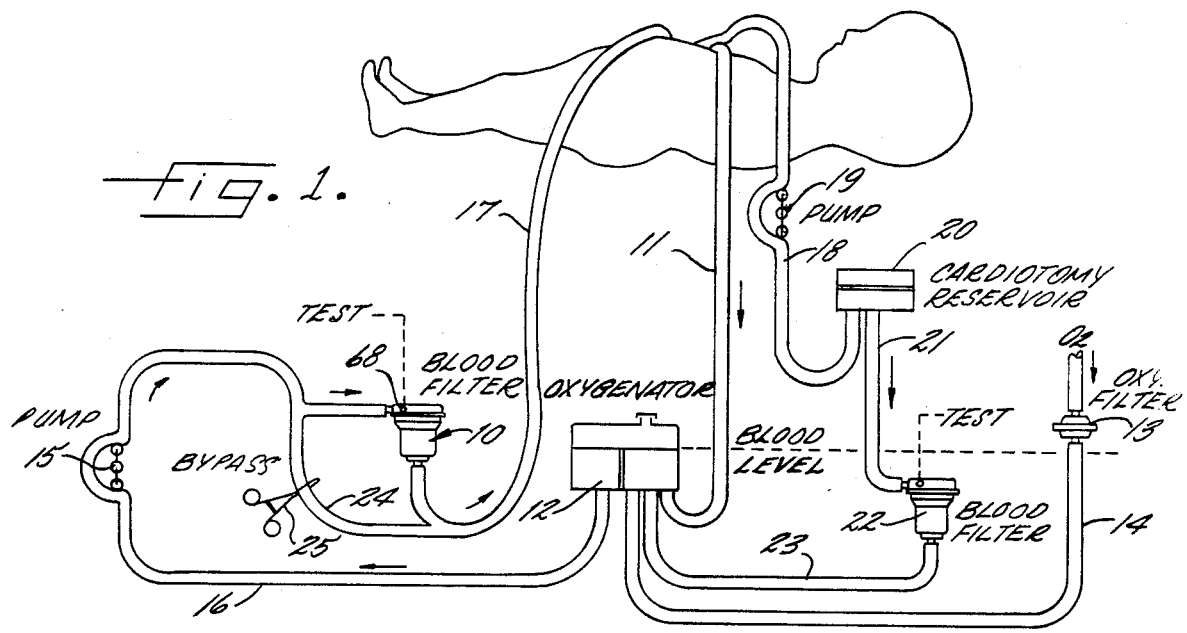
FIG. 1 is a schematic diagram of a cardiopulmonary bypass system employing a blood filter which embodies the present invention.

As shown in the drawings for purposes of illustration, the invention is embodied in an extracorporeal blood filter 10 such as is used in a cardiopulmonary bypass system during open heart surgery. Blood from the cardiovascular system of the patient flows through a tube 11 to an oxygenator 12 and oxygen also is delivered to the latter through a filter 13 and a tube 14 so that the oxygenator removes carbon dioxide from the blood and replaces it with oxygen. The perfusate is drawn from the oxygenator by a pump 15 through a tube 16 and is delivered to the filter 10 which removes microemboli including gas or air bubbles, fat emboli and aggregates formed from platelets, white blood cells, red blood cells and other debris. Usually, the filter is designed so that the smallest size of particulate removed is in the range of 25 to 50 microns, 40 microns being customary. From the filter, the filtered blood is returned to the cardiovascular system of the patient through a tube 17. Excess blood in the cavity in the patient where surgery is being performed is removed through a line 18 by a pump 19 and delivered to a cardiotomy reservoir 20. From the latter, the blood flows through a tube 21 to a filter 22, which may but need not be of the same construction as the filter 10, and then the blood flows through a tube 23 to the oxygenator 12 where it mixes with the blood from the patient's cardiovascular system. A bypass tube 24 around the filter 10 connects the tubes 16 and 17 and normally is closed by a clamp 25 which is released in an emergency when there is inadequate flow through the filter.

Figure 3:
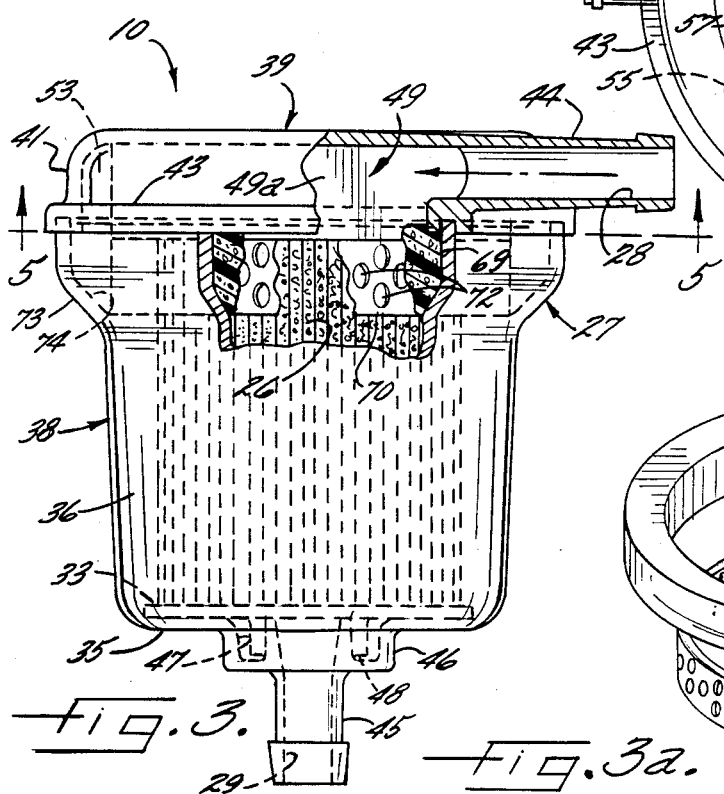
FIG. 3 is a sectional view taken along the line 3—3 in FIG. 2.

In general, the filter 10 includes an upright cylindrical filter element 26 (FIGS. 3 and 4) disposed within a generally cylindrical housing 27 which has an inlet passage 28 near its top and an outlet passage 29 at its bottom. The filter element includes a pleated screen made of a plastic material, polyesters and polyamides being examples, and the screen is wrapped around a perforated hollow core 30 (FIG. 4) made of a plastic material such as polypropylene. Thus, the filter element is a vertical cylinder with a central passage 31 extending along its axis and the upper ends of the filter element and the passage are closed by a cap 32 in the form of a disk molded from a plastic material such as polypropylene. A similar cap 33 closes the lower end of the filter element and is formed with a central opening 34 (FIG. 4) at the end of the passage 31 in the filter element and alined with the outlet passage 29 which, in this instance, extends through the bottom wall 35 of the housing. The filter element is disposed in a cylindrical chamber in the housing and is smaller in diameter than the side wall 36 of the chamber so that an annular space 37 is left between the side wall and the filter element. Thus, blood from the oxygenator 12 enters the space 37 and passes through the filter element from the outside and the filtered blood in the central passage 31 flows out through the outlet passage 29.

Herein, the housing 27 is made in two parts, that is, a body 38 and a cover 39 both molded from a plastic material such as polystyrene. The body includes the bottom and side walls 35 and 36 and is substantially coextensive in depth with the height of the filter element 26. The cover is a shallow cylinder and includes a generally flat top wall 40 and a downturned cylindrical side wall 41 and the open upper end of the body is received in an annular channel 42 (FIG. 4) formed in a flange 43 on the lower end of the cover side wall 41. The cover and the body are joined at the channel as by bonding or by a spin weld. The inlet passage 28 is formed in a nipple 44 which is integral with the cover and receives the end of the tube 16. Similarly, the outlet passage 29 is formed in a second nipple 45 which is molded integrally with the housing body and projects axially down from a boss 46 on the underside of the bottom wall 35. An annular groove 47 in the inside of the boss receives an annular extension 48 which surrounds the opening 34 in the cap 33 and which centrally locates the filter element in the body.

Preferably, at least some of the gas is removed from the blood before the latter reaches the filter element 26 and this is achieved in a chamber 49 (FIG. 3) located upstream of the filter element. In the present instance, this chamber is located in the cover 39 of the housing and is defined by the top wall 40 and the side wall 41 of the cover with the cap 32 on the top of the filter element serving as the bottom wall of the chamber. Some of the gas in the blood entering through the passage 28 separates from the blood while the blood is in the chamber 49 and is vented to the atmosphere. The blood then passes through an annular opening 50 (FIG. 4) in the bottom of the chamber to the space 37 around the filter element 26 and any remaining bubbles above a predetermined size, such as 40 microns, are removed by the filter element.

So long as the free gas in the blood enters the filter at a preselected limited rate, the flow of blood through the filter is steady and the filter element 26, being fully wetted with blood, is quite effective in removing the gas. If gross amounts of gas reach the annular space 37 and are presented to the filter element, however, the gas blocks the filter element, the pressure at the filter element rises and the gas is forced through the filter element to the patient's cardiovascular system. For example, a flow of 100 percent gas may be delivered to the filter in the event that the blood feed to the pump 15 is interrupted by reason of a tubing failure. Prior filters are incapable of venting such a flow of gas. Unless emergency measures are taken, therefore, the gas will pass through the filter and reach the patient. Morever, the accumulation of gas occurs rapidly and the emergency measures must be taken quickly. Thus, with a flow rate of six liters per minute, the housing 27 would be virtually filled with gas in about two seconds. Accordingly, a typical team of perfusionists using prior filters usually includes a technician who continually monitors the filter and is prepared to take appropriate steps as soon as the filter begins to fill with gas.

The present invention contemplates the provision of a new and improved blood filter 10 in which a significant portion of the gas in the blood is separated from the blood while still in the upstream chamber 49 and this gas, even in gross amounts, is automatically vented to the atmosphere without reaching the filter element 26. For this purpose, means is provided for causing the blood to flow in a generally circular path around the periphery of the upstream chamber and produce a centrifugal action which causes the blood to stay at the peripheral portion while the air moves to the center portion of the chamber and is vented through a hydrophobic membrane 51 (FIGS. 4 and 5) in the top wall 40 of the chamber. The membrane is designed so that it has a capacity to vent a full flow of air whereby only blood containing microemboli which can be filtered is presented to the filter element.

Figure 2:
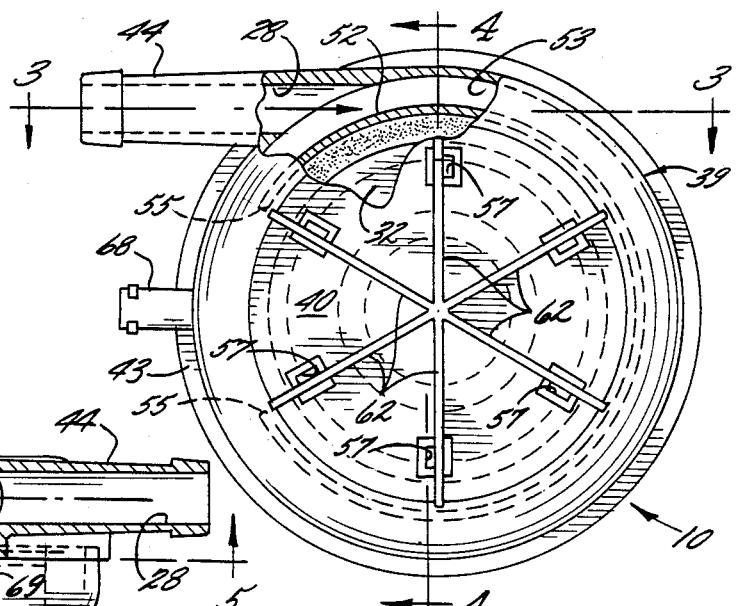
FIG. 2 is a top view of the filter with parts being broken away and shown in section.
Figure 4:
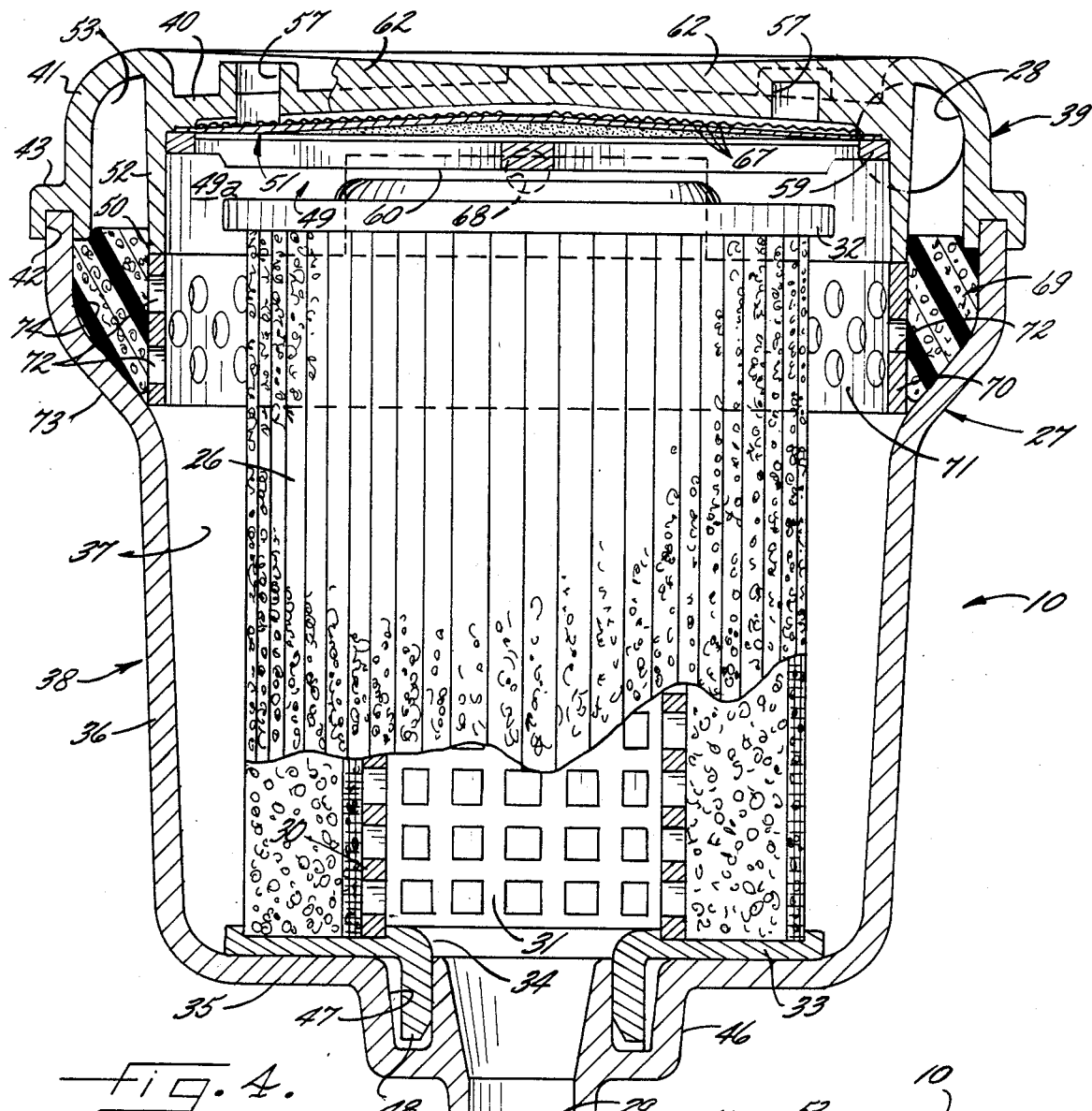
FIG. 4 is an enlarged sectional view taken along the line 4—4 in FIG. 2.
Figure 5:
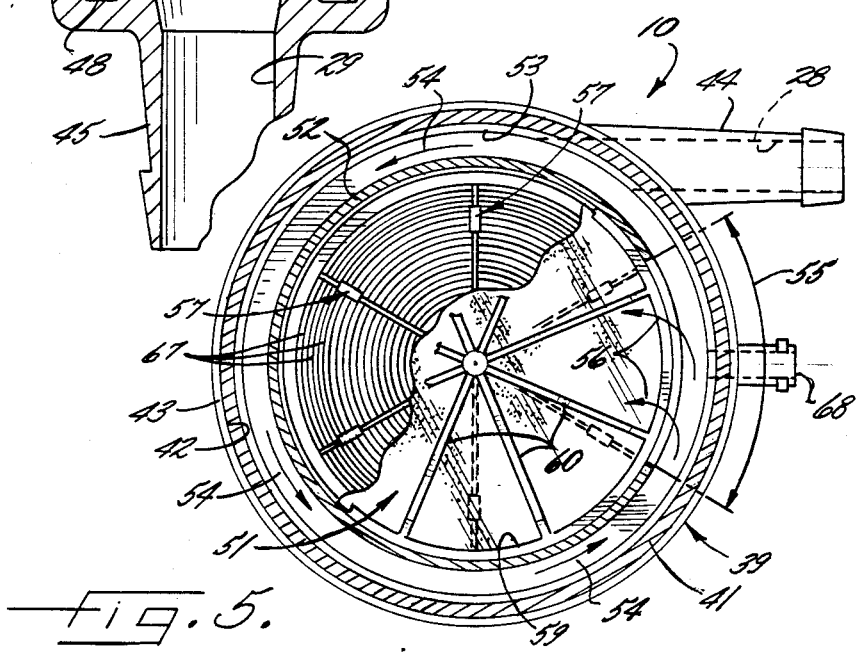
FIG. 5 is a sectional view taken along the line 5—5 in FIG. 3, parts being broken away and shown in section.

Herein, the means for causing the blood to flow in a circular path at the periphery of the upstream chamber 49 includes the nipple 44 which is arranged so that the inlet passage 28 is horizontal and opens through the side wall 41 of the cover 39 in a direction tangential to the side wall. As a result, the blood flows along the inside of the side wall at the periphery of the upstream chamber and, preferably, the circular flow of the blood at the periphery is maintained by an annular baffle 52 concentric with and spaced inwardly from the side wall. As shown in FIGS. 2 and 4, the baffle is formed integrally with the cover 29, extending downwardly from the top wall 40 thereof, and is generally coextensive with the side wall 41 so that it projects somewhat below the top of the filter element 26 and, with the side wall, forms a circular channel portion 53 in the chamber 49. The baffle extends for the major part of a full circle, beginning adjacent the inlet passage, and, herein, it begins slightly in advance of the passage and extends for 300 degrees. As the blood travels through the channel 53 as indicated by the arrows 54 in FIG. 5, the gas that is separated by centrifugal action moves against the outside of the baffle until it reaches an opening 55 defined by the ends of the baffle. At this point, the gas flows into the central portion 49a of the chamber 49 inside the baffle (see arrows 56) and is vented through the membrane 51 while the blood flows down into the annular space 37 and through the filter element.

Figure 6:
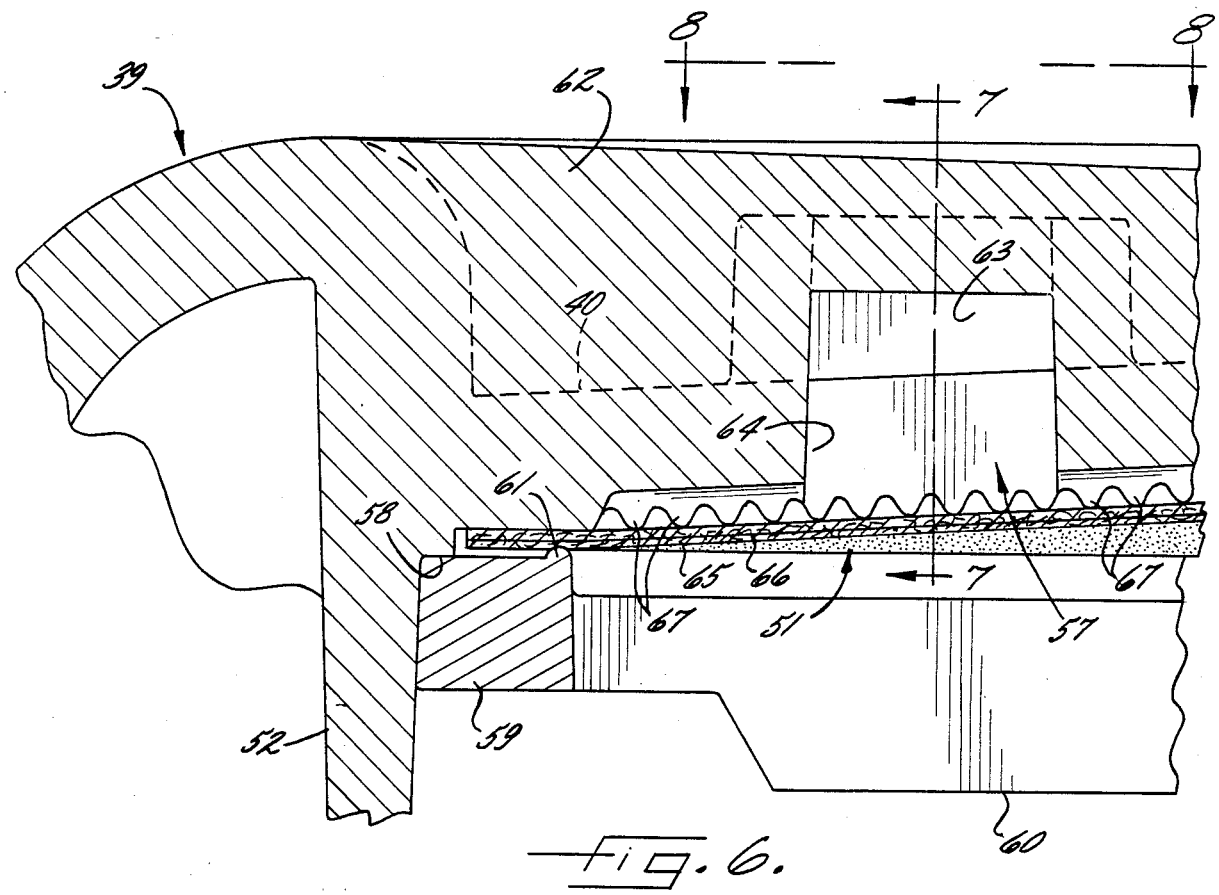
FIG. 6 is an enlarged fragmentary sectional view of the upper portion of the filter, the section being taken generally along the same line as FIG. 4.

To permit the relatively free flow of gas out of the upstream chamber 49, the hydrophobic membrane 51 is circular and is large enough to overlie substantially all of the center portion of the chamber 49 as defined by the baffle 52 so that the gas passes through the membrane and flows to vent holes 57 in the cover. In the present instance, the periphery of the membrane is clamped to a downwardly facing annular surface 58 (FIG. 6) on the underside of the cover by a plastic ring 59 which is bonded or otherwise suitably secured to the cover. A circular rib 61 upstanding from the ring bears against the membrane to produce the clamping action. Preferably, the ring also is used to support means for impeding and thus decreasing the circular flow in the center portion of the chamber 49 thus facilitating the flow of gas through the membrane 51. Herein, this means comprises a plurality of flat vanes 60 which are molded integrally with the ring and radiate from the center thereof. The vane underly the membrane and each is disposed in a vertical plane.

Figure 7:
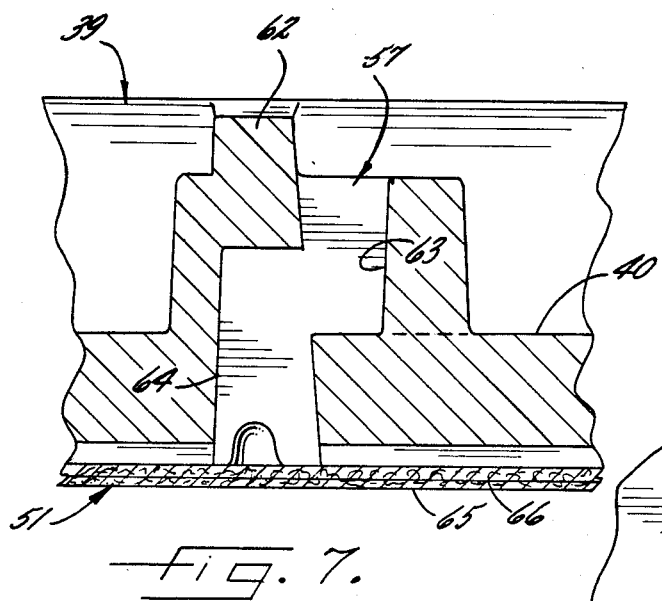
FIG. 7 is a fragmentary sectional view taken along the line 7—7 in FIG. 6.
Figure 8:
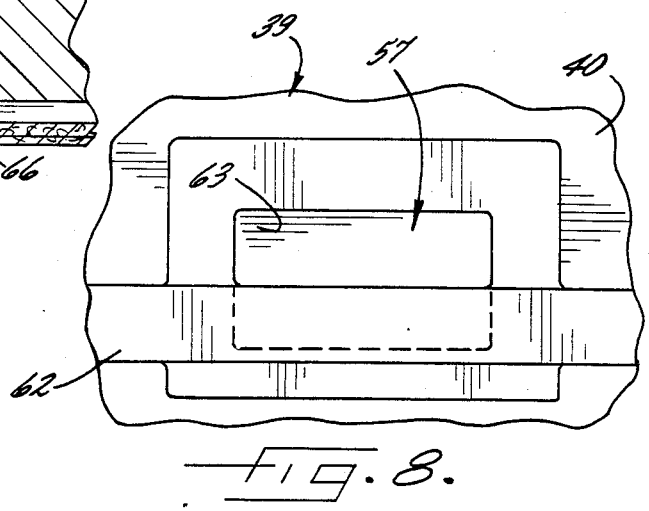
FIG. 8 is a fragmentary sectional view taken along the line 8—8 in FIG. 6.

Herein, there are six vent holes 57 equally spaced angularly around the top wall 40 of the cover 39 with each associated with a radial strengthening rib 62 molded integrally with the cover on top of the latter. As shown in FIG. 7, the upper portion 63 of each vent hole is offset laterally from the lower portion 64 to prevent a pointed instrument from being accidentally inserted through the hole and puncturing the membrane 51. Preferably, the latter is made up of a layer 65 of stretched highly crystalline polytetrafluorethylene, such as is known by the trademark TEFLON, heat sealed to a thin layer 66 of a substrate. The layer 65 is hydrophobic, that is, it is impermeable to liquid such as blood and is permeable to gas such as air. The layer 66 may be a thin porous paper such as the type conventionally used for making tea bags. The underside of the top wall of the cover is formed with a series of concentric circular ribs 67 which prevent the membrane from being pushed up flat against the top wall and thereby insure a free flow of air to the vent holes. If desired, the cover may be provided with opening 68 (FIG. 2) which may be closed or which may be connected to any desired test apparatus.

In accordance with another aspect of the invention, a body 69 of sponge material is treated with an antifoaming agent so as to capture small bubbles entrained in a liquid as the liquid is forced to flow down through the sponge and cause the bubbles to coalesce and form larger bubbles which break away from the sponge and rise against the flow of the liquid. As used in the filter 10, the sponge body is interposed in the opening 50 between the upstream chamber 49 and the space 37 around the filter element 26 so that the blood leaving the chamber passes through the sponge with the result that at least some of the smaller gas bubbles remaining in the blood are removed before the blood reaches the filter element 26. The sponge also brakes the rotational flow of the blood and dissipates the centrifugal forces which otherwise would tend to force the air bubbles rather than the blood toward the filter element. Herein, the sponge body is a strip of medical grade polyurethane foam with 20 to 50 pores per inch, 35 being suitable for present purposes, and the strip is wrapped around inside the upper end portion of the housing body 38 at the annular opening 50 in the upper chamber 49. The antifoaming agent may be a compound of silicone and silica such as is sold as "Medical Antifoam A" by Dow Corning Mfg. Co. and the sponge is treated by squeezing an inert liquid containing the compound through the sponge. As blood flows through the treated sponge, the silicone captivates small gas bubbles which, in turn, capture additional small bubbles while the silica breaks the film between two bubbles to create a larger one. Bubbles continue to grow in this manner until they become large enough to break away from the sponge and rise against the flow of blood.

Figure 3A:
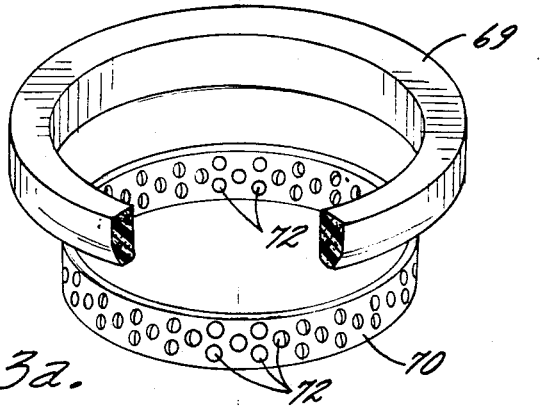
FIG. 3a is a fragmentary perspective view of the sponge body and its supporting ring.

Preferably, the sponge ring 69 is spaced radially outwardly of the filter element 26 by an annulus 70 to provide an annular passage 71 between the filter element and the annulus so that the larger bubbles produced by the sponge pass up through this passage to the center portion of the chamber 49 and out through the membrane 51 with that gas which is being removed in the upstream chamber. Herein, the annulus 70 is perforated as indicated at 72 in FIG. 3a and the larger air bubbles as formed in the sponge pass with the blood through the perforations to the passage 71 with the bubbles rising to the chamber 49 and the blood flowing down to the space 37 around the filter element. In the preferred embodiment, the annulus 70 is a cylindrical ring molded from the same plastic material as the body 27 and encircling the upper end of the filter element 26. The ring is concentric with the filter element and is the same diameter as the baffle 52 so as to constitute, in effect, an axial extension of the latter. To accommodate the sponge 69 and the ring 70, the upper end portion of the housing body 38 is flared as indicated at 73 to provide an inclined shoulder 74 upon which the ring rests. Thus, the ring is captivated between the baffle 52 and the shoulder 74 and holds the sponge in place in the flared portion 73 of the housing body.

With a blood filter 10 as described above, blood from the oxygenator 12 enters the upstream chamber 49 tangentially through the inlet passage 28 and flows in a circular path at the periphery of the cover 39 in the channel 53 as defined by the baffle 52 and the side wall 41 of the cover. That flow produces a centrifugal force which causes at least some of the gas bubbles in the blood, including any gross gas bubbles, to separate from the blood and move inwardly and through the opening 55 in the baffle to the central portion 49a of the upstream chamber. From there, the gas is vented to the atmosphere through the membrane 51 and the vent holes 57 and this venting is aided by the vanes 60 on the ring 59 which slow the rotational flow of the bubbles and thereby permit a more rapid flow of the gas through the membrane. The blood remaining in the channel 53 flows down through the sponge 69 and through perforated ring 70 and, while passing through the sponge, the smaller gas bubbles still remaining in the blood coalesce into larger bubbles. The latter together with the blood flow through the perforations 72 in the ring 70 to the passage 71 where the bubbles rise to the central portion of the upstream chamber 49 and are vented through the membrane 51. Due to its passing through the sponge, the rotational flow of the blood is braked so that the blood flows from the passage 71 to the outer surface of the filter element 26 without being impeded by gas bubbles. Any gas bubbles which remain in the blood at that time and which are larger than a predetermined size, such as 40 microns, are stopped by the filter element which also separates out other microemboli in the blood. The bubbles blocked by the filter element eventually coalesce with other bubbles to form larger bubbles which rise through the passage 71 to the chamber 49 for venting through the membrane. The filtered blood flows through the core 30 of the filter element and out through the outlet passage 29 for return to the patient.

We claim:

1. Apparatus for separating gas from blood before the blood passes through a filter, said apparatus comprising a housing defining a cylindrical chamber having top and bottom walls and a cylindrical side wall, said bottom wall having an annular opening extending generally around the periphery of said chamber and adapted to communicate with a filter, an annular baffle disposed in said chamber concentrically with said side wall and depending from said top wall to define an annular channel overlying said opening, an inlet communicating with said channel through said side wall and disposed to direct blood into the channel tangentially of the side wall whereby the blood flows in a generally circular path in the channel and generally downwardly out of said chamber through said opening, said circular flow producing a centrifugal action which causes the blood to flow at the outer periphery of said channel while gas entrained in the blood separates and moves inwardly, said baffle having an opening at a point where the baffle has defined a substantial part of a circle beginning near said inlet to permit the gas to enter the center portion of the chamber inside the baffle only after the blood has travelled a substantially full circle, at least one vent opening in the center portion of said top wall to permit gas in the center portion of said chamber to escape from the housing, and a hydrophobic membrane in said top wall covering said vent opening and extending over a substantial part of said center portion of said chamber to permit the automatic flow of gas but not blood out through said vent opening.

2. Apparatus as defined in claim 1 including a plurality of vanes depending from said top wall beneath said membrane to impede the circular flow of the gas in said center portion of said chamber and facilitate the flow of gas through the membrane.

3. Apparatus as defined in claim 2 in which said vanes extend generally radially from the center of said chamber toward said baffle and are generally equally spaced angularly around the chamber.

4. The apparatus of claim 1 which further comprises an annulus of sponge material including means for breaking the film between adjacent bubbles, said sponge material being disposed generally beneath said annular channel whereby at least some of the blood flowing in said annular chamber contacts said sponge material as the blood flows around said annular channel.

5. The apparatus of claim 4 wherein said baffle and sponge are arranged to assure at least some of the blood passes through the sponge in flowing generally downwardly out of said chamber.

6. A blood filter having, in combination, a housing having top, bottom and side walls and defining upper and lower chambers, at least said upper chamber being cylindrical, a cylindrical filter element disposed in said lower chamber and having a hollow interior, an outlet formed in said housing and communicating with the interior of said filter element, the outer surface of said filter element being spaced from the side wall of said housing to define an annular space surrounding the filter element, means closing the top of said filter element whereby blood from said upper chamber enters said annular space and flows through the filter element from the outside to the interior and out through said outlet, an inlet communicating with said upper chamber through the side wall of said housing and disposed to direct the blood generally tangentially of the upper chamber, an annular baffle disposed in said upper chamber concentrically with said side wall and depending from said top wall to define an annular channel for guiding blood which enters said upper chamber along a generally circular path at the periphery of the upper chamber, said circular flow producing a centrifugal action which causes the blood to flow to the periphery of the upper chamber and then to said annular space while gas entrained in the blood separates and moves inwardly, said baffle having an opening at a point where the baffle has defined a substantial part of a circle beginning near said inlet to permit the gas to enter to the center portion of the upper chamber inside the baffle only after the blood has travelled a substantially full circle, at least one vent opening in the center portion of said top wall to permit the gas in the center portion of said chamber to escape from said housing, and a hydrophobic membrane in said top wall covering said vent opening and extending substantially over said center portion of said upper chamber to permit the automatic flow of gas but not blood out through said vent opening.

7. A blood filter as defined in claim 6 including a plurality of vanes depending from said top wall beneath said membrane to impede the circular flow of the gas in said center portion of said upper chamber and facilitate the flow of gas through the membrane.

8. A blood filter as defined in claim 7 in which said vanes extend generally radially from the center of said upper chamber toward said baffle and are generally equally spaced around the chamber.

9. A blood filter as defined in claim 8 including a ring encircling and rigid with the outer ends of said vanes, said ring being rigidly secured to said top wall and said membrane being clamped between the ring and the top wall.

10. The apparatus of claim 6 which further comprises an annulus of sponge material including means for breaking the film between adjacent bubbles, said sponge material being disposed generally beneath said annular channel whereby at least some of the blood flowing in said annular chamber contacts said sponge material as the blood flows around said annular channel.

11. The apparatus of claim 10 wherein the baffle and sponge are arranged to assure at least some of the blood passes through the sponge in flowing generally downwardly out of said chamber.

12. Apparatus for separating gas from blood, said apparatus comprising, a housing defining a first cylindrical chamber having top and bottom walls and a cylindrical side wall, said bottom wall having an annular opening extending around the periphery of said chamber, an annular baffle disposed in said chamber concentrically with said side wall to define an annular channel overlying said opening, an inlet communicating with said channel through said side wall and disposed to direct blood into the channel tangentially of the side wall whereby the blood flows in a generally circular path in the channel and then out of said chamber through said opening, said circular flow producing a centrifugal action which causes the blood to flow at the outer periphery of said channel while gas entrained in the blood separates and moves inwardly, said baffle having an opening to permit the gas to enter the center portion of the chamber inside the baffle, venting means in the center portion of said top wall to permit gas in the center portion of said chamber to escape from the housing, a hydrophobic membrane in said top wall covering said venting means and extending substantially over said center portion of said chamber to permit the flow of gas out through said venting means, said housing defining a second cylindrical chamber coaxial with and disposed beneath said first chamber, a cylindrical filter element disposed in said second chamber coaxially therewith and having a hollow interior, an outlet formed in said housing and communicating with the interior of said filter element, the outer surface of said filter element being spaced from the outside of said second chamber to define an annular space alined and communicating with said annular channel, an annulus of sponge material disposed in the upper end portion of said annular space and extending around the periphery of said second chamber whereby blood flows from the channel through the sponge annulus to said space and hence to said filter element, said sponge annulus including means for causing gas bubbles in the blood to coalesce and form larger gas bubbles as the blood flows through said sponge annulus, and a ring holding said sponge annulus radially spaced outwardly from said filter element to define an annular passage whereby said larger gas bubbles exit said sponge annulus and move through said passage to said center portion of said first chamber where they are vented through said membrane.

13. Apparatus as defined in claim 12 in which said ring is perforated whereby blood and said larger bubbles flow out of said sponge annulus through the perforations in the ring and into said annular passage.

14. A blood filter having, in combination, a housing having top, bottom and side walls and defining upper and lower cylindrical chambers, a cylindrical filter element disposed in said lower chamber and having a hollow interior, an outlet formed in said bottom wall and communicating with the interior of said filter element, the outer surface of said filter element being spaced from the side wall of said housing to define an annular space surrounding the filter element, means closing the top of said filter element whereby blood from said upper chamber enters said annular space and flows through the filter element from the outside to the interior and out through said outlet, an annulus of sponge material disposed in the upper end of said annular space and extending around the periphery of said housing, means in said upper chamber for directing blood to said sponge annulus whereby the blood flows through the latter to said annular space, said sponge annulus including means for causing gas bubbles in the blood to coalesce and form larger gas bubbles as the blood flows through said sponge annulus, means forming an annular passage between said sponge annulus and said filter element whereby said large gas bubbles exit the sponge annulus and move through said annular passage to said upper chamber, and means permitting gas in said upper chamber to be vented to atmosphere.

15. A blood filter as defined in claim 14 which said means for forming said annular passage is a ring encircling said filter element and radially spaced from the latter whereby the ring and the filter element define the annular passage and said sponge annulus is disposed between the ring and the side wall of said housing.

16. A blood filter as defined in claim 15 in which said ring is perforated whereby blood and said larger gas bubbles flow out of said sponge annulus through the perforations in the ring and into said annular passage.

17. A blood filter as defined in claim 16 in which said means for causing the blood to coalesce is a compound of silicone and silica with the silicone capturing smaller gas bubbles in said sponge annulus and said silica causing the film between adjacent bubbles to break and form larger bubbles.

* * * * *